United States Patent
Lenges et al.

(10) Patent No.: US 7,214,828 B2
(45) Date of Patent: May 8, 2007

(54) DURABLE COATING COMPOSITIONS CONTAINING NOVEL ASPARTIC AMINE COMPOUNDS

(75) Inventors: Christian Peter Lenges, Wilmington, DE (US); Alan Martin Allgeier, Oak Park, CA (US); Robert John Barsotti, Franklinville, NJ (US); Patrick Henry Corcoran, Cherry Hill, NJ (US); Laura Ann Lewin, Greenville, DE (US); Stefan Reinartz, Wilmington, DE (US)

(73) Assignee: E. I. duPont de Nemours and Company, Wilmington, DE (US)

( * ) Notice: Subject to any disclaimer, the term of this patent is extended or adjusted under 35 U.S.C. 154(b) by 7 days.

(21) Appl. No.: 11/303,075

(22) Filed: Dec. 14, 2005

(65) Prior Publication Data

US 2006/0155148 A1  Jul. 13, 2006

Related U.S. Application Data

(60) Provisional application No. 60/636,434, filed on Dec. 15, 2004.

(51) Int. Cl.
C07C 211/00 (2006.01)

(52) U.S. Cl. ...................................................... 564/454
(58) Field of Classification Search ................. 564/454
See application file for complete search history.

(56) References Cited

U.S. PATENT DOCUMENTS

| | | | | |
|---|---|---|---|---|
| 5,126,170 A | * | 6/1992 | Zwiener et al. | 427/385.5 |
| 5,236,741 A | * | 8/1993 | Zwiener et al. | 427/385.5 |
| 5,243,012 A | * | 9/1993 | Wicks et al. | 528/58 |
| 5,412,056 A | * | 5/1995 | Zwiener et al. | 528/73 |
| 5,516,873 A | * | 5/1996 | Hicks et al. | 528/60 |
| 5,561,214 A | * | 10/1996 | Yeske et al. | 528/363 |
| 5,580,945 A | * | 12/1996 | Wade et al. | 528/49 |
| 6,005,062 A | * | 12/1999 | Hansen et al. | 528/68 |

\* cited by examiner

*Primary Examiner*—Samuel Barts

(57) ABSTRACT

A coating composition comprising a binder of
   a. polyisocyanate crosslinking agent;
   b. an isocyanate-reactive component having at least one compound having the following formula:

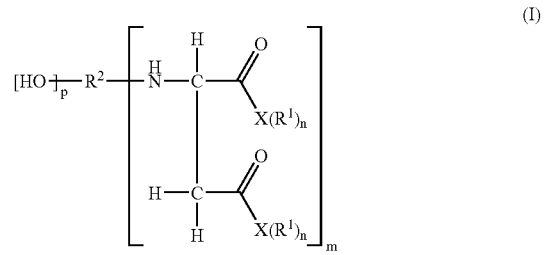

(I)

wherein
$X$, $R^1$, $R^2$, $p$, $m$ and $n$ are described in the specification, or isomer or mixture of isomers thereof, two component compositions, articles coated with the novel composition and novel hydroxy amines are also part of the invention.

1 Claim, No Drawings

DURABLE COATING COMPOSITIONS CONTAINING NOVEL ASPARTIC AMINE COMPOUNDS

CROSS-REFERENCE TO RELATED APPLICATION

This application claims the benefit of U.S. Provisional Application Ser. No. 60/636,434 filed on Dec. 15, 2004 which are hereby incorporated by references in its entirely.

FIELD OF THE INVENTION

This invention is directed to coating compositions, in particular, to coating compositions that are useful as exterior clear finishes for automobiles and trucks.

BACKGROUND OF THE INVENTION

The finishing system of choice presently being used on the exterior of automobiles and trucks comprises a clear coating applied over pigmented base coating that is applied over a primer coating. The clear coating provides protection, in particular, protection from weathering, to the pigmented base coating and improves the appearance of the overall finish, in particular, provides improved gloss and distinctness of image. The primer coating provides adhesion to the substrate and, in particular, provides resistance to stone chipping. When used in refinishing of automobile and truck bodies, the clear coating is required to have an acceptable "pot life" and reasonably short cure time period to allow for further processing or handling of the vehicle without damaging the finish. The term "pot life" means the period of time after a coating is mixed with a catalyst or a crosslinking agent in which the composition remains at a sprayable viscosity.

The following U.S. patents: U.S. Pat. No. 5,516,873, U.S. Pat. No. 5,126,170, U.S. Pat. No. 5,243,012, U.S. Pat. No. 5,236,741, U.S. Pat. No. 5,412,056, U.S. Pat. No. 5,580,945, and U.S. Pat. No. 6,005,062, show a variety of coating composition that contain polyaspartic acid derivatives but these compositions do not have a property balance of acceptable pot life and rapid curing time to form a sufficiently hard finish to allow additional handling and processing of a coated vehicle or work piece after the coating composition has been applied.

To improve the rate curing, EP 0939091 uses novel amine compounds, for example, the reaction product of 4,4'-methylene-biscyclohexanamine with two moles of diethyl maleate. However, coating composition formulated with these reactive amines do not have the desired balance of acceptable pot-life and the desired cure rate after application to an object while maintaining or improving on the desired properties of the resulting finish. In an effort to improve pot life, solvents and catalysts have been used but solvents have a deleterious effect on VOC (volatile organic content) emissions, which is undesirable and catalyst can result in deterioration of film properties, such as durability. It is, therefore, desired to find a class of amine functional compounds for the reaction with isocyanates, which form coating compositions that overcome these problems and form acceptable finishes for automotive and truck substrates.

EP 0743333 describes the use of simple hydroxy aspartates in the preparation of hydroxy-functional polyhydantion prepolymers and their use as co-reactants for blocked polyisocyanates or aminoplast resins. The use of hydroxy-aspartates as the nucleophilic component in coating systems with polyisocyanates is not described. In U.S. Pat. No. 5,561,214, the use of hyperbranched polyaspartate ester polymers is described based on the selfcondensation of hydroxy-aspartates and these polymers are used as binder resins in coating systems.

The novel composition of this invention utilizes novel reactive amine compound having less reactive hydroxy functional groups as a nucleophilic component with a polyisocyanate crosslinking agent that form coating compositions having an optimum balance of pot life and curing time and form finishes, in particular, clear and primer finishes useful for automobiles and trucks. The clear coatings have excellent properties, such as, hardness, gloss, durability, weatherability, and in particular resistance to UV (ultraviolet light) degradation, particularly when reinforced with ultraviolet light absorbers and screeners and hindered amine light stabilizers. The primer coatings exhibit excellent adhesion to metal substrates, in particular, aluminum and steel substrates, and provide for excellent stone chip resistance.

These compounds may be used as part of the binder component or as the sole nucleophilic component in a two component coating mixture. When used as the sole nucleophile, especially environmentally friendly coating compositions may be formulated with low or even zero VOC (volatile organic content). The advancement achieved with the novel coating compositions of this invention over the prior art is based on effectively balancing the pot life of the coating mixture with the cure characteristics using the unique structural characteristics of new aspartic-hydroxyl compositions in combination with polyisocyanates. It is surprising that the use of a nucleophilic component based on compounds of this invention which contain both aspartate and hydroxyl functional groups in a curing reaction with polyisocyanates leads to a high productivity coating system with good general coating properties while meeting desired environmental goals of eliminating or reducing VOC of a coating composition while maintaining a good pot life.

SUMMARY OF THE INVENTION

A coating composition comprising a binder of
a. polyisocyanate crosslinking agent;
b. an isocyanate-reactive component having at least one compound having the following formula:

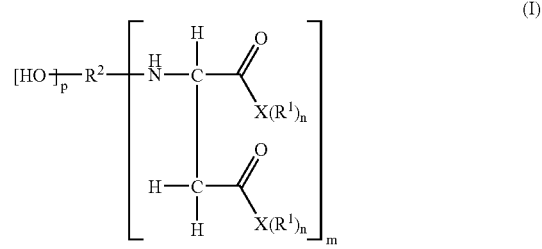

(I)

wherein
X can be independently O or N; if X equals O, n equals 1 and if X equals N, n equals 2;

wherein
$R^1$ is independently selected from H, a $C_1$ to $C_{20}$ linear or branched alkyl group, a $C_5$ to $C_{16}$ cycloaliphatic group, a phenyl group, a $C_6$ to $C_{20}$ aryl group substituted with a $C_1$ to $C_{12}$ alkyl group, preferred groups for $R^1$ are ethyl, propyl, n-butyl, sec-butyl, cyclohexyl;

wherein m, on average, equals 1, 2 or 3, preferably, m, on average, equals 1;

wherein $R^2$ comprises the hydrocarbon radical obtained by removing the amino and hydroxyl groups from an amino alcohol, wherein p, on average, equals 1, 2 or 3, preferably, p, on average, equals 1.

Two component composition formulated with the above constituents and substrates, such as, automotive and truck bodies and parts coated with the novel composition containing the hydroxy amine compounds are also part of this invention.

DETAILED DESCRIPTION OF THE INVENTION

The features and advantages of the present invention will be more readily understood, by those of ordinary skill in the art, from reading the following detailed description. It is to be appreciated those certain features of the invention, which are, for clarity, described above and below in the context of separate embodiments, may also be provided in combination in a single embodiment. Conversely, various features of the invention that are, for brevity, described in the context of a single embodiment, may also be provided separately or in any sub-combination. In addition, references in the singular may also include the plural (for example, "a" and "an" may refer to one, or one or more) unless the context specifically states otherwise.

The use of numerical values in the various ranges specified in this application, unless expressly indicated otherwise, are stated as approximations as though the minimum and maximum values within the stated ranges were both preceded by the word "about." In this manner, slight variations above and below the stated ranges can be used to achieve substantially the same results as values within the ranges. Also, the disclosure of these ranges is intended as a continuous range including every value between the minimum and maximum values.

All patents, patent applications and publications referred to herein are incorporated by reference in their entirety.

A typical auto or truck body is produced from a steel sheet or a plastic or a composite substrate. For example, the fenders may be of plastic or a composite and the main portion of the body of steel. If steel is used, it is first treated with an inorganic rust-proofing compound, such as, zinc or iron phosphate and then a primer coating is applied generally by electrodeposition. Typically, these electrodeposition primers are epoxy-modified resins crosslinked with a polyisocyanate and are applied by a cathodic electrodeposition process. Optionally, a primer can be applied over the electrodeposited primer, usually by spraying, to provide better appearance of a base coating or a mono coating applied over the primer and to improve the adhesion of such coatings to the primer or both of the above. A mono coating of a pigmented coating composition then can be applied but preferably, a pigmented base coating with a clear top coating is applied to form a clear coat/color coat finish on the truck or automobile body or auto or truck part. Usually, after application, each of the coatings is cured by baking at an elevated temperature. It is generally known that a clear top coating can be applied over the base coating and both coatings cured together at an elevated temperature.

When refinishing automobile and truck bodies, the original OEM topcoat is usually sanded and a primer or sealer coat applied and then a mono coat or a basecoat/clear coat is applied. These coatings are usually cured at ambient temperatures or at slightly elevated temperatures, such as, 40 to 100° C.

A "clear coating composition" for automotive use is a composition that forms a transparent finish upon curing and typically has a DOI (distinctness of image) of more than 70 and a 20° gloss of more than 70. These clear coatings provide a glossy in depth appearance to the finish on the automobile or truck and therefore, are required to have good gloss and distinctness of image. Also, the clear finish also provides a protective finish that is durable and resistant to scratching, marring and chipping and also provides resistance to weathering, in particular to U.V. degradation and photo-oxidation.

A "matte clear coating composition" can also be used, for example for the interior of an automobile or truck. These matte finishes have a substantially lower gloss, for example, a 20° gloss of 20 or less and very low DOI.

Typical "primer compositions" provide adhesion to a substrate and for the novel compositions of this invention provide excellent adhesion to bare metal substrates, such as, steel and aluminum, and to treated metal substrates, such as galvanized steel, and provide a surface to which the topcoat, such as, a pigmented mono coat or the basecoat of a base coat clear coat finish.

The term "binder" as used herein refers to the film forming constituents of the composition that include the isocyanate reactive component, i.e., having functional groups that are reactive with isocyanates and comprising active hydrogen, and optional polymeric and/or oligomeric components, polyisocyanate crosslinking agents and optional reactive diluents, such as, ketimines and aldimines and optional acrylic non-aqueous dispersions. Solvents, pigments, catalysts, rheology modifiers, antioxidants, U.V. absorbers, hindered amine light stabilizers, antioxidants, in particular disubstituted phenolic compounds, hydroperoxide decomposers, leveling agents, antifoaming agents, anti-cratering agents, adhesion promoting agents are not included in the term.

Molecular weight (both number and weight average) is determined by gel permeation chromatography utilizing a high performance liquid chromatograph supplied by Hewlett-Packard, Palo Alto, Calif. and unless otherwise stated the liquid phase used was tetrahydrofuran and the standard was polymethylmethacrylate or polystyrene.

"Tg" (glass transition temperature) is in ° C. and determined by Differential Scanning Calorimetry or calculated according to the Fox Equation.

Typically, the binder of the novel composition comprises 20 to 80% by weight, based on the weight of the binder, of the isocyanate reactive component or hydroxyl containing aspartic acid derivative and 20 to 80% by weight, based on the weight of the binder, of a polyisocyanate crosslinking agent. The stochiometric ratio of isocyanate functionality to isocyanate reactive component is 0.5 to 3.0, preferably, 0.8 to 2.0 and most preferably, 1.0 to 1.5. Optionally, the binder can contain up to 75% by weight, preferably, 5 to 60% by weight, and most preferably, 5 to 30% by weight, based on the weight of the binder, of a polymeric or oligomeric component or both wherein the component contains groups that are reactive with the polyisocyanate crosslinking agent. One preferred binder composition contains 25 to 50%, by weight of the isocyanate reactive component, 5 to 30% by weight of the polymeric or oligomeric component or both and 20 to 70% by weight of a polyisocyanate, wherein the sum of all of the components of the binder is 100%. Another preferred binder composition contains the isocyanate reactive component or hydroxyl containing aspartic acid derivative as the sole nucleophilic component that is reactive with the polyisocyanate.

Particular advantages of the novel coating composition of this invention is that it provides a protective clear finish that has an excellent balance between pot life and cure characteristics once applied to the object. Also, the resulting finish has good gloss and distinctness of image that provides an excellent appearance. The finish hardens in a reasonably short time after application and has excellent weatherability, in particular resistance to U.V. degradation and photo-oxidation when properly reinforced with the appropriate additives. When the novel composition is used to refinish automobiles and trucks, it has excellent adhesion to metal substrates and cures to a tack free state in a relatively short period of time under ambient temperatures or under slightly elevated drying temperatures, for example, 40 to 100° C., that allows a coated vehicle to be moved or further processed without damage to the finish.

The novel composition of this invention can contain pigments and is useful as a pigmented mono-coat topcoat, as a pigmented base coat of a base coat/clear coat finish or as a primer or primer surfacer, which cures in a relatively short period of time to allow for subsequent application of topcoats, basecoat/clear coats or monocoats. The novel composition can also be used for OEM (original equipment manufacture) of automobiles, trucks and parts thereof.

The novel composition may be solvent based and has a solids content of film forming binder of 20 to 90% by weight, preferably, 40 to 80% by weight. It may be possible to formulate a 100% solids composition using the compounds of this invention. In addition, reactive diluents can be used to formulate high solids compositions and applied at high viscosities, e.g., using airless spray equipment or can be used as a putty.

An aqueous liquid carrier, which typically is water but may contain other liquids, may be used in place of the solvent. Before application, a sufficient amount of liquid usually is added, for example, water or solvents, to reduce the composition to a spray viscosity. In the event that the novel coating composition is an aqueous composition, the pH of the composition typically is 6.0 to 10.0 and preferably, 7.5 to 8.5.

The isocyanate reactive component of the novel composition is an aspartic acid derivative and has the formula (I)

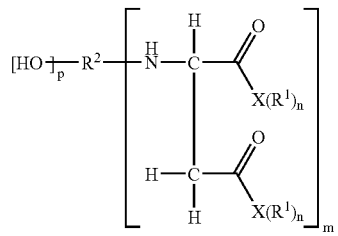

wherein
X can be independently O or N; if X equals O, n equals 1 and if X equals N, n equals 2;

wherein
$R^1$ is independently selected from H, a $C_1$ to $C_{20}$ linear or branched alkyl group, a $C_5$ to $C_{16}$ cycloaliphatic group, a phenyl group, a $C_6$ to $C_{20}$ aryl group substituted with a $C_1$ to $C_{12}$ alkyl group, preferred groups for $R^1$ are ethyl, propyl, n-butyl, sec-butyl, cyclohexyl;

wherein
m, on average, equals 1, 2 or 3, preferably, m, on average, equals 1;

wherein
$R^2$ comprises the hydrocarbon radical obtained by removing the amino and hydroxyl groups from an amino alcohol, wherein
p, on average, equals 1, 2 or 3, preferably, p, on average, equals 1.

The aspartic acid derivatives suitable for the coating compositions of this invention may be prepared by reacting optionally substituted maleic or fumaric acid derivatives with amino alcohols.

The isocyanate reactive compounds of this invention are prepared in a reaction of the amino alcohol substrate with a maleic or fumaric acid derivative of the general formula (II)

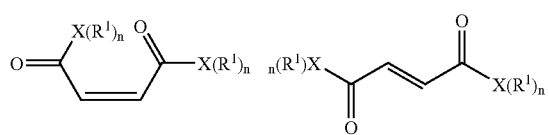

with $R^1$ and X as described above.

For the synthesis of the isocyanate reactive components of this invention useful maleic or fumaric acid derivatives are for example dimethyl maleate, diethyl maleate, di-n-butyl maleate, di-sec-butyl maleate, dicyclohexyl maleate, tetraethylmaleamide, tetrapropylmaleamide, (Z)-1,4-di(piperidin-1-yl)but-2-ene-1,4-dione, diethylmaleamide, (Z)-methyl 3-(butylcarbamoyl)acrylate, (Z)-ethyl 3-(dipropylcarbamoyl)acrylate and the corresponding fumaric acid derivatives. The preparation of the isocyanate reactive components of this invention from the indicated starting materials may be carried out in a temperature range of 0 to 100° C. The mole-ratios of starting materials used of these reactions are such that for each primary amine functional group at least one and preferentially one equivalent of maleic or fumaric acid derivative is used. Optionally, starting materials which are used in excess in this reaction can be separated from the product mixture using methods known to those skilled in the art, such as distillation or chromatography. The reaction can be carried out using the starting materials directly or in the presence of a solvent such as methanol, ethanol, propanol, tetrahydrofuran, dioxan, toluene, xylenes, acetonitrile, dimethylformamide, pyridine or mixtures of such solvents.

The choice of the specific structure of the amino alcohol used on this invention is critical to the overall coatings properties of the coatings compositions of this invention. The amino alcohols used in this invention are described in the following embodiments.

Suitable amino alcohols for the preparation of the aspartic acid derivatives of this invention as described in this first embodiment are based on general formula (IV):

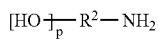 (IV)

wherein
  p has a value of 1 to 3, preferably 1,
  and $R^2$ represents a hydrocarbyl radical obtained by removing the amino and hydroxyl groups from the of formula (IV) amino alcohol.

Suitable amino alcohols include ethanolamine, 1-amino-2-hydroxypropane, 1,3-propanolamine, (a commercial product from BASF Intermediates), the isomeric butanolamines, 1,5-pentanolamine and 1,6-hexanolamine (both commercial products from BASF Intermediates), 2-(hydroxyethoxy)ethylamine (product by BASF Intermediates), isomeric mixtures of amino-cyclooctanol (as described in DE 1077658), isomeric mixtures of amino-cyclododecanol (as described as byproducts in WO 03027052), 4-aminomethylcyclohexanemethanol (as described in U.S. Pat. No. 3,137,727 and in U.S. Pat. No. 3,143,570), 4-aminomethylcyclohexanepropanol, (4-(aminomethyl)-3-ethylcyclohexyl)methanol, 4-[(4-amino-cyclohexyl)-methyl]-cyclohexanol (as described in DE 1468779).

Furthermore, other suitable amino alcohols for the preparation of the aspartic acid derivatives of this invention are described in this second embodiment with $-R^2-[OH]_p$ in general formula (IV) described by formula (V):

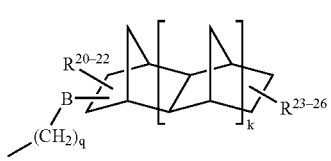 (V)

wherein
  the exact point of attachment and orientation of the $-CH_2-B-$ group (which also connects to the amine nitrogen atom) and the $R^{20}-R^{26}$ groups to the norbornane skeleton can vary and mixtures of compounds and isomers are commonly utilized by this invention;
  the $-(CH_2)_q-$ group in Formula (V) attaches to the amine group in Formula (IV);
  k equals 0, 1 or 2 and, when k equals 1 or 2, the additional bridging $CH_2$ group(s) may be on the same or opposite side with respect to the first bridging $CH_2$ group;
  B equals $(-(CH_2)_t-(CH)-(CH_2)_s-)_r$, r=0 or 1, s+t=1 to 16, with the $-(CH)-$ group connecting to the $-(CH_2)_q-$ group, in which B forms a ring connecting to the norbornane skeleton in place of one of $R^{20}$, $R^{21}$ or $R^{22}$ substituents;
  $R^{20}$, $R^{21}$, and $R^{22}$ can be the same or different and are each independently H, a $C_1$ to $C_{20}$ linear or branched alkyl group;
  q is equal to 1, 2, 3, or 4;
  $R^{23}$, $R^{24}$, $R^{25}$ and $R^{26}$ can be the same or different and are each independently H, a $C_1$ to $C_{20}$ linear or branched alkyl group;
  with the proviso that at least one substituent independently selected from $R^{23}$, $R^{24}$, $R^{25}$ and $R^{26}$ is a $-OH$ group, or a $C_1$ to $C_{20}$ linear or branched alkyl group bearing a hydroxyl group.

Exemplary cycloaliphatic compounds of structure (V) which correspond to $-R^2-[OH]_p$ of general formula (IV) include those represented by Formulae (VI)–(XIX) as shown below.

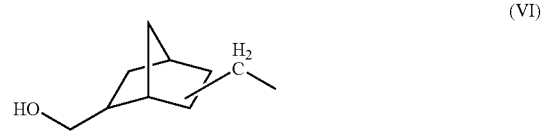 (VI)

 (VII)

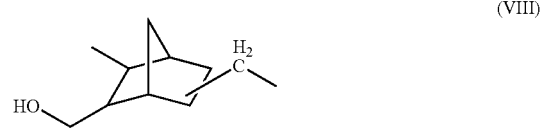 (VIII)

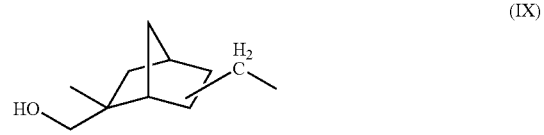 (IX)

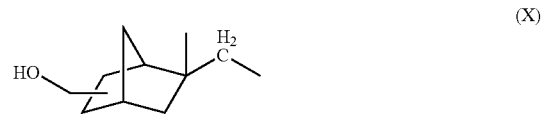 (X)

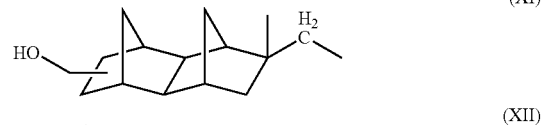 (XI)

 (XII)

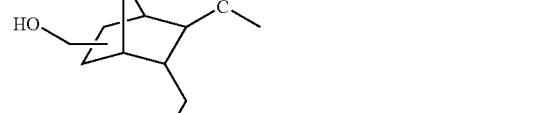 (XIII)

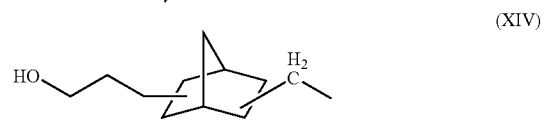 (XIV)

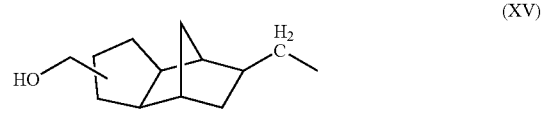 (XV)

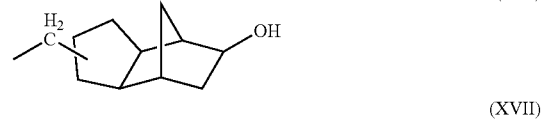 (XVI)

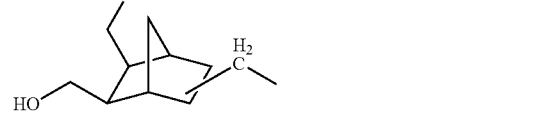 (XVII)

-continued

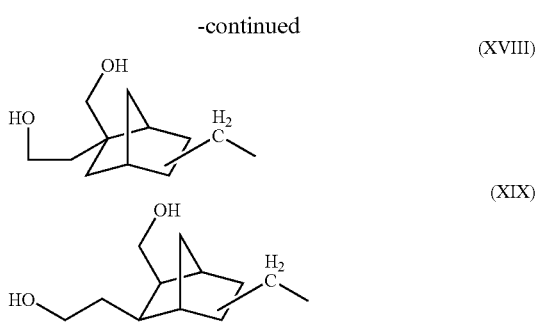

and isomers of any of the above.

According to general structure (IV), the above listed cycloaliphatic alcohol radicals in Formulae (VI)–(XIX) each connect to an $NH_2$ group to represent novel cycloaliphatic amino alcohol compounds that are used in this invention.

The norbornene derivatives used as starting materials in this embodiment of the invention contain a substituted norbornene (bicyclo[2.2.1]heptene) fragment which may be further reacted by hydrocyanation or by hydroformylation. Products of these processes are, for example, nitrile aldehyde norbornane derivatives. These substituted norbornene starting materials can be prepared using procedures known in the literature. Typical examples are described in Organic Chemistry, $3^{rd}$ Edition, Peter Vollhardt and Neil Schore, N.Y., Freeman and Company, 1998, pg 600, or in U.S. Pat. No. 5,861,528, U.S. Pat. No. 6,100,323, or U.S. Pat. No. 5,284,929.

Certain cycloaliphatic amino alcohol compounds (for example (VIII), (IX), (XIV)–(XIX)) may be derived from the nitrile-ester precursor. These cycloaliphatic nitrile derivatives can be prepared as described in filed U.S. patent application Ser. No. 10/760,779, filed Jan. 19, 2004. The corresponding cycloaliphatic amine derivatives can be prepared as described in filed U.S. patent application Ser. No. 10/760,778, filed Jan. 19, 2004. The entire disclosure of these applications is incorporated herein by reference. These nitrile ester compounds may be hydrogenated to the corresponding amino alcohol compounds while the hydrogenation of the carboxylic acid or ester functional group may be carried out following procedures outlined in JP54145650, JP00355564.

Certain cycloaliphatic amino alcohol compounds, for example compound (XII), may be derived from a hydroboration—oxidation reaction as described for example in Chemische Berichte (1989), 122(5), 975–84 followed by a hydrogenation reaction.

Certain cycloaliphatic amino alcohol compounds, for example compound (VI), (VII), (X), (XII)—(XIV), (XVI), may be derived from a hydroformylation process in combination with a hydrogenation process.

For example, compound (VI) may be derived from 5,6-cyano-bicyclo-[2.2.1]-heptane-2-carboxaldehyde which may be derived from cyano-bicyclo-[2.2.1]-heptane in a hydroformylation reaction. A process for this transformation has been described in U.S. Pat. No. 2,956,977, EP82-104243, JP60072844, WO2001007382. Other derivatives as listed above may be prepared using a similar process. However, it is preferred to produce the composition of the invention by the process disclosed below. The amino-alcohols of this invention may be formed in a hydrogenation reaction by the process disclosed below using nitrile, aldehyde or other carboxylic acid derivatives as precursors.

A process of preparing the amino-alcohol compounds of this invention (for example (VI), (VII), (X), (XII)–(XIV), (XVI)) may be carried out in a two step process of hydroformylation followed by hydrogenation. Alternatively, both reaction steps may be combined into one process step in which the hydroformylation and the hydrogenation of the formed aldehyde functional group occur in the same reaction step. The hydroformylation process comprises contacting the precursor cycloaliphatic nitrile derivative, with a gas mixture of CO and hydrogen in the presence of a catalyst at a temperature in the range from about 50° C. to about 150° C., preferably about 80° C. to about 110° C., under a pressure that can accommodate the temperature range, preferably in the range of from about 50 to about 10,000 kPa for a period of from about 1 minute to about 72 hours.

The hydroformylation process comprises reacting a monoethylenically unsaturated nitrile compound with a source of CO and $H_2$ in the presence of a catalyst precursor composition comprising a transition metal selected from the group of Co, Rh, Ru, Ir, Pd, and Pt, and at least two monodentate or one multidentate ligand, typical examples are triphenylphosphite or triphenylphosphine.

The reaction conditions of the hydroformylation process according to this invention are in general the same as used in a conventional process, described, for example, in U.S. Pat. No. 4,769,498, which is incorporated herein by reference and will be dependent on the particular starting ethylenically unsaturated organic compound. For example, the temperature can be from room temperature to 200° C., preferably from 50–120° C. The pressure may vary from atmospheric pressure to 20 MPa, preferably from 0.15 to 10 MPa and more preferably from 0.2 to 1 MPa. The pressure is, as a rule, equal to the combined hydrogen and carbon monoxide partial pressure. Extra inert gases may however be present. The molar ratio of hydrogen to carbon monoxide is generally between 10 to 1 and 1 to 10, preferably between 6 to 1 and most preferably 1 to 2.

The amount of rhodium compound is not specially limited, but is optionally selected so that favorable results can be obtained with respect to catalyst activity and economy. In general, the concentration of rhodium in the reaction medium is between 10 and 10,000 ppm and more preferably between 50–500 ppm, calculated as the free metal.

The molar ratio of monodentate or multidentate phosphorus ligand to rhodium is not specially limited, but is optionally selected so that favorable results can be obtained with respect to catalyst activity, aldehyde selectivity, and process economy. This ratio generally is from about 0.5 to 100 and preferably from 1 to 10 (moles of ligand to moles of metal).

The choice of solvent is not critical provided the solvent is not detrimental to catalyst, reactant and product. The solvent may be a mixture of reactants, such as the starting unsaturated compound, the aldehyde product and/or by-products. Suitable solvents include saturated hydrocarbons, such as, kerosene, mineral oil or cyclohexane, ethers, such as, diphenyl ether, tetrahydrofuran or a polyglycol, ketones, such as, methyl ethyl ketone and cyclohexanone, nitriles, such as, methylglutaronitrile, valeronitrile, and benzonitrile, aromatics, such as, toluene, benzene and xylene, esters, such as, methyl valerate and caprolactone, dimethyl-formamide, and sulfones, such as, tetramethylenesulfone. The reaction may also be conducted with reactants and products in the gas phase.

Preferably, when a liquid reaction medium is used, the reaction mixture is agitated, such as by stirring or shaking.

The hydroformylation process according to the invention can be performed as described below:

The preferred temperature range is from about 50° C. to about 180° C., most preferably from about 90° C. to 110° C. The temperature must be chosen so as to maintain all of the reactants and products in the vapor phase, but low enough to prevent deterioration of the catalyst. The particular preferred temperature depends to some extent on the catalyst being used, the olefinic compound being used, and the desired reaction rate. The operating pressure is not particularly critical and can conveniently from about 1–10 atmospheres (101.3 to 1013 kPa). The pressure and temperature combination must be chosen so as to maintain reactants and products in the vapor phase.

The method for making certain amino alcohols of the present invention involves a hydrogenation process of molecules containing aldehyde and nitrile moieties, either alone or as mixtures of isomers or mixtures of compounds. The compounds or mixtures of compounds may be contacted with hydrogen in the presence of a catalyst, optionally, in the presence of a solvent and/or a promoter to yield molecules comprising alcohol and amine moieties. The process comprises the reduction of both the aldehyde and the nitrile moiety and may be conducted in one reaction step or in two sequential reaction steps, with isolation of molecules containing alcohol and nitrile moieties.

During the hydrogenation process the feed (i.e., molecules containing aldehyde and nitrile moieties either alone or in mixtures of isomers) is contacted with hydrogen. The mole ratio of hydrogen to feed is not critical as long as sufficient hydrogen is present to produce the desired products. Hydrogen is preferably used in excess. Hydrogen pressures are generally in the range of about 340 kPa–17240 kPa (50–2500 psig), with 689 to 8274 kPa (100–1000 psig) preferred. The hydrogenation process can be conducted at temperatures from 40° C. to about 180° C., preferably from 55° C. to about 100° C.

Preferred catalysts for hydrogenating the feed comprise one or more elements from the series of transition metals, particularly useful are cobalt, nickel, copper, ruthenium, rhodium, palladium and combinations thereof. The hydrogenation catalyst may also comprise one or more elements in addition to the transition metals mentioned above, including but not limited to chromium, titanium, gold, iron and platinum. The hydrogenation catalyst can also be in the form of an alloy, including a solid solution of two or more elements. The hydrogenation catalyst can also be a homogeneous catalyst capable of hydrogenating aldehydes and nitriles, e.g., rhodium or ruthenium complexes bearing phosphine or phosphite ligands.

The transition metal for hydrogenation can also be supported on an inorganic support, such as, alumina, magnesium oxide and combinations thereof. The metal can be supported on an inorganic support by any means known to one skilled in the art such as, for example, impregnation, co-precipitation, ion exchange, or combinations of two or more thereof. The metal can be reduced before the hydrogenation reaction by any means known to one skilled in the art such as, for example, pretreatment with hydrogen, formaldehyde or hydrazine.

The hydrogenation catalyst can be present in any appropriate physical shape or form. It can be a homogeneous catalyst, a heterogenized homogeneous catalyst or it can be in fluidizable forms, powders, extrudates, tablets, spheres or combinations of two or more thereof. The hydrogenation catalyst may be in sponge metal form, for example, the Raney® nickels and Raney® cobalts. The molar ratio of hydrogenation catalyst to feed can be any ratio as long as the ratio can catalyze the hydrogenation. The weight ratio of hydrogenation catalyst to feed is generally in the range of from about 0.0001:1 to about 1:1, preferably about 0.001:1 to about 0.1:1. If the catalytic element is supported on an inorganic support or is a portion of an alloy or solid solution, the catalytic element is generally present in the range of from about 0.1 to about 60, preferably about 1 to about 50, and most preferably about 2 to about 50 weight percent based on the total hydrogenation catalyst weight.

The hydrogenation can optionally be conducted in the presence of a solvent. Suitable solvents include those known in the art as useful for hydrogenation reactions. Examples of these are amines, aliphatic alcohols, aromatic compounds, ethers, esters (including lactones), and amides (including lactams). Specific examples of solvents include: ammonia, toluene, tetrahydrofuran, methanol, ethanol, any isomeric propanol, any isomeric butanol and water. Preferred solvents include tetrahydrofuran, ammonia and methanol. It will be appreciated that the solvent may serve to reduce the viscosity of the system to improve fluidity of the catalyst in the reaction vessel, as well as serve to remove the heat of reaction from the feed and products. The solvent may be present in a range of 1% to 75% by weight of the total reaction mixture, excluding the catalyst, preferably from 10% to 50%.

Optionally, a promoter may be used in the hydrogenation process to alter the rate of the reaction and/or to alter the selectivity of the reaction. Suitable promoters include water, mineral acids, alkali or alkaline earth metal hydroxides, quaternary ammonium hydroxides, quaternary ammonium cyanides, quaternary ammonium fluorides, and combinations of these. Promoters may be present at from 10 ppm to 3% by weight of the total reaction mixture, excluding the catalyst, preferably from 50 ppm to 1.5%.

Preferably the process is conducted in two sequential steps. In the first step the aldehyde moieties are hydrogenated to primary alcohol moieties. The preferred aldehyde hydrogenation conditions comprise a ruthenium supported on carbon catalyst, 50–80° C., and 689–3447 kPa (100–500 psig). The preferred nitrile hydrogenation conditions comprise a catalyst of the sponge nickel or cobalt type, 70–100° C., and 3447–8274 kPa (500–1200 psig). Commercially available sponge metal catalysts are promoted or un-promoted Raney® Ni or Raney® Co catalysts that can be obtained from the W. R. Grace and Co. (Chattanooga, Tenn.), or alternative sponge metal catalysts available, for example, from Activated Metals Corporation (Sevierville, Tenn.) or Degussa (Parsippany, N.J.). Commercially available ruthenium on carbon catalysts or other supported catalysts are available from Engelhard Corporation (Iselin, N.J.) or Degussa (Parsippany, N.J.).

Preferred aspartic-hydroxyl compositions of this invention are shown in formulae (XX)–(XXXIII):

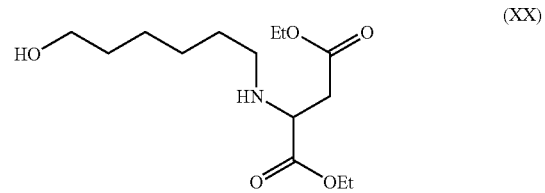

(XX)

-continued
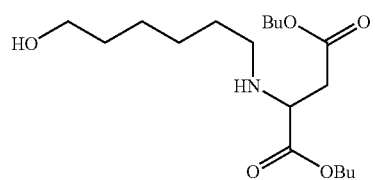
(XXI)
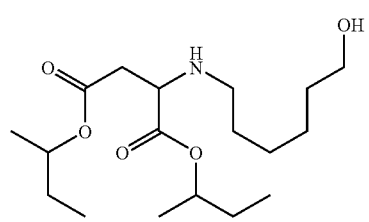
(XXII)
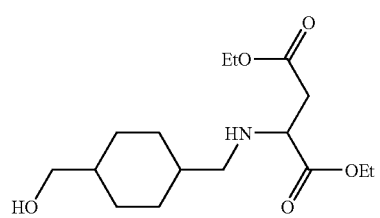
(XXIII)
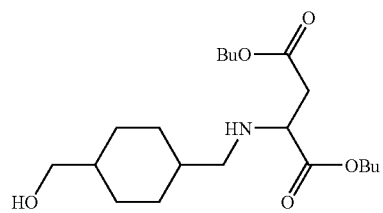
(XXIV)
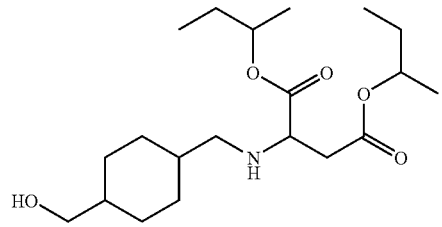
(XXV)
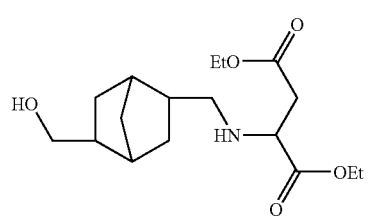
(XXVI)
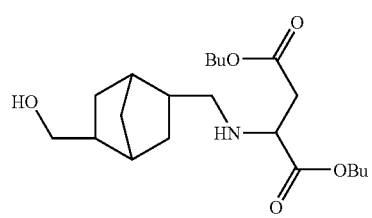
(XXVII)
-continued
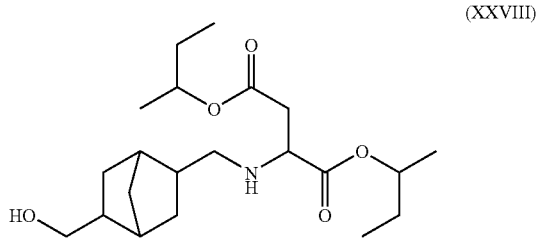
(XXVIII)
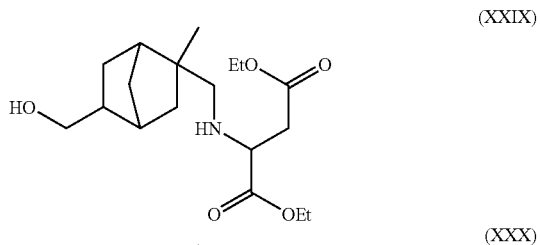
(XXIX)
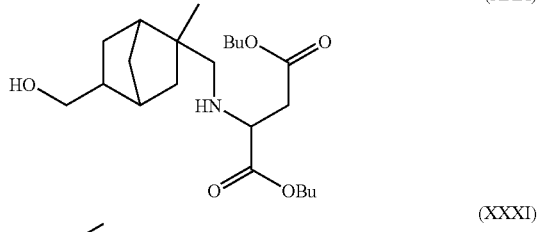
(XXX)
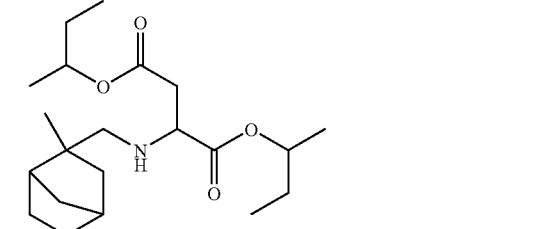
(XXXI)
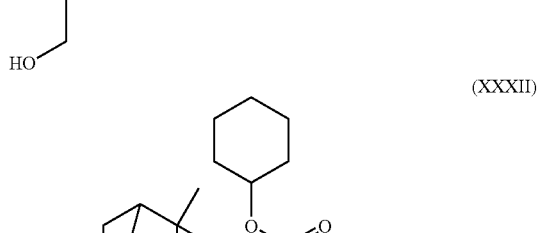
(XXXII)
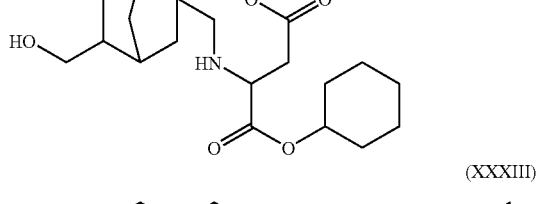
(XXXIII)
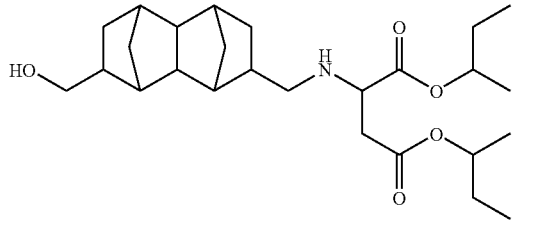
and isomers of any of the above.

The novel coating composition can contain optional polymeric components. These components have groups that are reactive with isocyanate and can be used in an amount of up to 75% by weight, preferably, 1–60% by weight, based on the weight of the binder. One preferred polymeric component is an acrylic polymer. Typically useful acrylic polymers have a number average molecular weight of about 5,000 to 50,000, a Tg of 10 to 80° C. and contain moieties, such as, hydroxyl, carboxyl, glycidyl and amino groups. Typically useful acrylic polymers are those known in the art and are polymers of two or more of the following: linear alkyl (meth)acrylates having 1 to 12 carbon atoms in the alkyl group, cyclic or branched alkyl (meth)acrylates having 3 to 12 carbon atoms in the alkyl group including isobornyl (meth)acrylate, hydroxy alkyl (meth)acrylates having 1 to 4 carbon atoms in the alkyl group, glycidyl (meth)acrylate, hydroxy amino alkyl (meth)acrylates having 1 to 4 carbon atoms in the alkyl group, and can contain styrene, alpha methyl styrene, vinyl toluene, (meth)acrylonitrile (meth) acryl amides, (meth)acrylic acid, (meaning both acrylic acid and methacrylic acid) trimethoxysilylpropyl (meth)acrylate and the like.

Preferred are hydroxy functional acrylic polymers having a hydroxy equivalent weight of 300 to 1300 and are polymers of hydroxy alkyl (meth)acrylates and one or more of the aforementioned monomers. One preferred hydroxy containing acrylic polymer contains 35 to 50% by weight styrene, 15 to 25% by weight ethylhexyl methacrylate and 15 to 20% by weight isobornyl methacrylate and 20 to 30% by weight hydroxyethyl methacrylate. A particularly preferred acrylic polymer contains 37% styrene, 20% by weight 2-ethylhexyl methacrylate and 17.5% by weight of isobornyl methacrylate and 25.5% by weight hydroxyethyl methacrylate.

Acrylic oligomers having a number average molecular weight of 300 to 3,000 of the aforementioned monomeric components also can be used as the optional polymeric component. By using monomers and reactants well known to those skilled in the art, these oligomers can have the one or more of the following groups that are reactive with isocyanate: hydroxyl, carboxyl, glycidyl, amine, aldimine, phosphoric acid and ketimine. Typically useful acrylic oligomers are disclosed in FA 1048 Ser. No. 10/617,585 filed Jul. 11, 2003, Publication No. U.S. 2004-001009 published on Jan. 15, 2004, which is hereby incorporated by reference.

Polyesters can also be used as the optional polymeric component, such as, hydroxyl or carboxyl terminated or hydroxyl or carboxyl containing polyesters. The following are typically useful polyesters or ester oligomers: polyesters or oligomers of caprolactone diol and cyclohexane dimethylol, polyesters or oligomers of tris-hydroxy ethylisocyanurate and caprolactone, polyesters or oligomers of trimethylol propane, phthalic acid or anhydride and ethylene oxide, polyesters or oligomers of pentaerythritol, hexahydrophthalic anhydride and ethylene oxide, polyesters or oligomers of pentaerythritol, hexahydrophthalic anhydride and butylene oxide, such as those shown in U.S. Pat. No. 6,221,494 B1 which is hereby incorporated by reference.

The aforementioned polyesters and oligomers can be reacted with an organic isocyanate to form urethane polymers and oligomers that can be used as the optional polymeric component in the novel composition.

One useful urethane oligomer that can used in the novel composition is formed by reacting an aliphatic polyisocyanate with an aliphatic or cycloaliphatic monohydric alcohol and subsequently reacting the resulting composition with a hydroxy functional aliphatic carboxylic acid until all of the isocyanate groups have been reacted. One useful polyurethane oligomer comprises the reaction product of the isocyanurate of hexane diisocyanate, cyclohexanol and dimethylol propionic acid. A water dispersible oligomer can be formed using conventional techniques known to those skilled in the art.

Optionally, an oligomeric component having a number average molecular weight of 300 to 3,000 having reactive groups that crosslink with an isocyanate, where the reactive groups are hydroxyl, carboxyl, glycidyl, amine, aldimines, phosphoric acid, ketimine and any mixtures thereof can be added to the novel composition.

Typically useful organic polyisocyanates crosslinking agents that can be used in the novel composition of this invention include aliphatic polyisocyanates, cycloaliphatic polyisocyanates and isocyanate adducts. Examples of suitable aliphatic and cycloaliphatic polyisocyanates that can be used include the following: 4,4'dicyclohexyl methane diisocyanate, ("$H_{12}$MDI"), trans-cyclohexane-1,4-diisocyanate, 1,6-hexamethylene diisocyanate ("HDI"), isophorone diisocyanate, ("IPDI"), other aliphatic or cycloaliphatic di-, tri- or tetra-isocyanates, such as, 1,2-propylene diisocyanate, tetramethylene diisocyanate, 2,3-butylene diisocyanate, octamethylene diisocyanate, 2,2,4-trimethyl hexamethylene diisocyanate, dodecamethylene diisocyanate, omega-dipropyl ether diisocyanate, 1,3-cyclopentane diisocyanate, 1,2 cyclohexane diisocyanate, 1,4 cyclohexane diisocyanate, 4-methyl-1,3-diisocyanatocyclohexane, dicyclohexylmethane-4,4'-diisocyanate, 3,3'-dimethyl-dicyclohexylmethane 4,4'-diisocyanate, polyisocyanates having isocyanurate structural units, such as, the isocyanurate of hexamethylene diisocyanate and the isocyanurate of isophorone diisocyanate, the adduct of 2 molecules of a diisocyanate, such as, hexamethylene diisocyanate, uretidiones of hexamethylene diisocyanate, uretidiones of isophorone diisocyanate and a diol, such as, ethylene glycol, the adduct of 3 molecules of hexamethylene diisocyanate and 1 molecule of water, allophanates, trimers and biurets of hexamethylene diisocyanate, allophanates, trimers and biurets of isophorone diisocyanate and the isocyanurate of hexane diisocyanate.

Tri-functional isocyanates also can be used, such as, Desmodur® N 3300, trimer of hexamethylene diisocyanate, Desmodur® 3400, trimer of isophorone diisocyanate, Desmodur® 4470 trimer of isophorone diisocyanate, these trimers are sold by Bayer Corporation. A trimer of hexamethylene diisocyanate sold as Tolonate® HDT from Rhodia Corporation is also suitable.

An isocyanate functional adduct can be used, such as, an adduct of an aliphatic polyisocyanate and a polyol. Also, any of the aforementioned polyisocyanates can be used with a polyol to form an adduct. Polyols, such as, trimethylol alkanes, particularly, trimethylol propane or ethane can be used to form an adduct.

The novel composition can contain 1 to 30% by weight, based on the weight of the binder of acrylic NAD (nonaqueous dispersed) resins. These NAD resins typically are high molecular weight resins having a crosslinked acrylic core with a Tg between 20 to 100° C. and attached to the core are low Tg stabilizer segments. A description of such NADs is found in Antonelli et al. U.S. Pat. No. 4,591,533 and in Barsotti et al. U.S. Pat. No. 5,763,528 which patents are hereby incorporated by reference.

Optionally, a catalyst may be used in the novel composition to reduce curing time and temperature and allow curing of the coating at ambient temperatures. Useful catalysts include those known to the person skilled in the art, like, alkyl carboxylic acids having 1 to 12 carbon atoms in the alkyl group, such as, acetic acid, formic acid, glycolic acid; aromatic acids, such as, benzoic acid; and oligomers having pendant acid groups.

The coating composition optionally may also include a catalytically active amount of one or more tin or tertiary amine catalysts for accelerating the curing process. Generally, catalytically active amounts of the catalyst in the coating composition range from about 0.001 percent to about 5 percent, preferably from 0.005 percent to 2 percent, more preferably from 0.01 percent to 1 percent, all in weight percent based on the weight of the binder. A wide variety of catalysts can be used, such as, tin compounds, including stannous octoate, stannic chloride, butyltin trichloride, dibutyl tin dilaurate (DBTDL), dibutyltin-bis(dodecyl mercaptan), di(2-ethylhexyl)tin oxide, dibutyl tin diacetate, dibutyltin sulfonamide, and dibutyltin dibutoxide (DBTO); tertiary amines, such as, triethylamine, tributylamine, N-methylmorpholine, N-ethylmorpholine, N,N,N',N'-tetramethylethylene diamine, pentamethyldiethylene triamine, 1,4-diazabicyclo[2.2.2]octane (DABCO), N-methyl-N'-(dimethylaminoethyl)-piperazine, N,N-dimethylbenzylamine, N,N-dimethylcyclohexylamine, N,N-diethylbenzylamine, bis(N,N-diethylaminoethyl) adipate. N,N,N',N'-tetramethyl-1,3-butanediamine, N,N-dimethyl-1,3-phenylethylamine, 1,2-dimethylimidazole, 1-methylimidazole, 2-methylimidazole. Especially also the combination of tertiary amines and tin compounds may be used as catalyst. One of the commercially available catalysts, sold under the trademark, Fastcat® 4202 dibutyl tin dilaurate by Elf-Atochem North America, Inc. Philadelphia, Pa., is particularly suitable. Commercially available tertiary amines include 1,2-dimethylimidazole and 1-methylimidazole by BASF AG, 1,4-diazabicyclo[2.2.2]octane (DABCO® crystalline) by Air Products, and N,N.N',N'-tetramethylethylene diamine (TOYOCAT-TE) by TOSOH. Other catalyst may also be used for this reaction such as, Al, Ti, Bi or Zr catalyst, K-Kat 348 (bismuth carboxylate), K-Kat 4205 (Zirconium chelate 2,5-pentanedione), K-Kat 5218 (Aluminum chelate complex), K-Kat XC-6212 (Zirconium complex), acid catalysts such as para toluene sulfonic acid or dodecyl benzene sulfonic acid, typically available from King Industries. The use of these described catalysts and especially the combination of these catalysts allows the formulation of the amino-alcohol oligomers of this invention with the desired improved potlife along with the desired cure characteristics and the desired film properties.

When used as a clear coating or mono-coat composition, the novel composition optionally contains about 0.1 to 5% by weight, based on the weight of the binder, of ultraviolet light absorbers. Typically useful ultraviolet light absorbers include hydroxyphenyl benzotriazols, such as, 2-(2-hydroxy-5-methylphenyl)-2H-benzotriazole, 2-(2-hydroxy-3,5-di-tert.amyl-phenyl)-2H-benzotriazole, 2[2-hydroxy-3,5-di(1,1-dimethylbenzyl)phenyl]-2H-benzotriazole, reaction product of 2-(2-hydroxy-3-tert.butyl-5-methyl propionate)-2H-benzotriazole and polyethylene ether glycol having a weight average molecular weight of 300, 2-(2-hydroxy-3-tert.butyl-5-iso-octyl propionate)-2H-benzotriazole; hydroxyphenyl s-triazines, such as, 2-[4((2,-hydroxy-3-dodecyloxy/tridecyloxypropyl)-oxy)-2-hydroxyphenyl]-4,6-bis(2,4-dimethylphenyl)-1,3,5-triazine, 2-[4(2-hydroxy-3-(2-ethylhexyl)-oxy)-2-hydroxyphenyl]-4,6-bis(2,4-dimethylphenyl) 1,3,5-triazine, 2-(4-octyloxy-2-hydroxyphenyl)-4,6-bis(2,4-dimethylphenyl)-1,3,5-triazine; hydroxybenzophenone U.V. absorbers, such as, 2,4-dihydroxybenzophenone, 2-hydroxy-4-octyloxybenzophenone, and 2-hydroxy-4-dodecyloxybenzophenone.

When used as a clear coating or mono-coat composition, the novel composition optionally contains about 0.1 to 5% by weight, based on the weight of the binder, of a di-substituted phenol antioxidant or a hydroperoxide decomposer. Typically useful antioxidants include tetrakis[methylene(3,5-di-tert-butylhydroxy hydrocinnamate)]methane, octadecyl 3,5-di-tert-butyl-4-hydroxyhydrocinnamate, tris (2,4-di-tert-butylphenyl) phosphite, 1,3,5-tris(3,5-di-tert-butyl-4-hydroxybenzyl)-1,3,5-triazine-2,4,6(1H,3H,5H)-trione and benzenepropanoic acid, 3,5-bis(1,1-dimethylethyl)-4-hydroxy-$C_7$–$C_9$ branched alkyl esters. Typically useful hydroperoxide decomposers include Sanko® HCA (9,10-dihydro-9-oxa-10-phosphenanthrene-10-oxide), triphenyl phosphate and other organo-phosphorous compounds, such as, Irgafos® TNPP from Ciba Specialty Chemicals, Irgafos® 168, from Ciba Specialty Chemicals, Ultranox® 626 from GE Specialty Chemicals, Mark PEP-6 from Asahi Denka, Mark HP-10 from Asahi Denka, Irgafos® P-EPQ from Ciba Specialty Chemicals, Ethanox 398 from Albemarle, Weston 618 from GE Specialty Chemicals, Irgafos® 12 from Ciba Specialty Chemicals, Irgafos® 38 from Ciba Specialty Chemicals, Ultranox® 641 from GE Specialty Chemicals and Doverphos® S-9228 from Dover Chemicals.

When used as a clear coating or mono-coat composition, the novel composition optionally contains about 0.1–5% by weight, based on the weight of the binder, of hindered amine light stabilizers. Typically useful hindered amine light stabilizers include N-(1,2,2,6,6-pentamethyl-4-piperidinyl)-2-dodecyl succinimide, N(1acetyl-2,2,6,6-tetramethyl-4-piperidinyl)-2-dodecyl succinimide, N-(2hydroxyethyl)-2,6,6,6-tetramethylpiperidine-4-ol-succinic acid copolymer, 1,3,5 triazine-2,4,6-triamine, N,N'''-[1,2-ethanediybis[[[4,6-bis [butyl(1,2,2,6,6-pentamethyl-4-piperidinyl)amino]-1,3,5-triazine-2-yl]imino]-3,1-propanediyl]]bis[N,N'''-dibutyl-N', N'''-bis(1,2,2,6,6-pentamethyl-4-piperidinyl)], poly-[[6-[1, 1,3,3-tetramethylbutyl)-amino]-1,3,5-trianzine-2,4-diyl][2, 2,6,6-tetramethylpiperidinyl)-imino]-1,6-hexane-diyl[(2,2, 6,6-tetramethyl-4-piperidinyl)-imino]), bis(2,2,6,6-tetramethyl-4-piperidinyl)sebacate, bis(1,2,2,6,6-pentamethyl-4-piperidinyl)sebacate, bis(1-octyloxy-2,2,6,6-tetramethyl-4-piperidinyl)sebacate, bis(1,2,2,6,6-pentamethyl-4-piperidinyl)[3,5bis(1,1-dimethylethyl-4-hydroxy-phenyl)methyl]butyl propanedioate, 8-acetyl-3-dodecyl-7,7,9,9,-tetramethyl-1,3,8-triazaspiro(4,5)decane-2,4-dion, dodecyl/tetradecyl-3-(2,2,4,4-tetramethyl-2l-oxo-7-oxa-3,20-diazal dispiro(5.1.11.2)henicosan-20-yl) propionate.

To form a coating composition that has a high level of weatherability and resistance to UV degradation, a combination of above described ultraviolet light absorbers, antioxidants and hindered amine light stabilizers can be used.

Typically, the composition is a solvent based composition and any of the known organic solvents may be used to form the coating composition. Typical solvents include aromatic hydrocarbons, such as, toluene, xylene; ketones, such as, acetone, methyl ethyl ketone, methyl isobutyl ketone, methyl amyl ketone and diisobutyl ketone; esters, such as, ethyl acetate, n-butyl acetate, isobutyl acetate; and mixtures of any of the above.

The novel coating composition may also include other conventional formulation additives, such as, wetting agents, leveling and flow control agents, for example, Resiflow®S (polybutylacrylate), BYK® 320 and 325 (high molecular weight polyacrylates), BYK® 347 (polyether-modified siloxane), rheology control agents, such as, fumed silica, defoamers, surfactants and emulsifiers to help stabilize the composition. Other additives that tend to improve mar resistance can be added, such as, silsesquioxanes and other silicate-based micro-particles.

The coating composition of this invention can be used as a clear coat that is applied over a pigmented base coat that may a pigmented version of the composition of this invention or another type of a pigmented base coat. The clear coating can be in solution or in dispersion form.

Typically, a clear coating is then applied over the base coating before the base coating is fully cured, a so called "wet-on-wet process", and the base coating and clear coating are then fully cured at ambient temperatures or can be cured by heating to elevated temperatures of 40° C. to 170° C. for 15 to 45 minutes. If used in refinishing vehicles, the base coat may be allowed to "dry to the touch" at ambient temperature conditions or under warm air before the clear coating is applied. The base coating and clear coating preferably have a dry coating thickness ranging from 25 to 75 microns and 25 to 100 microns, respectively. Also, the composition can be used as a matte clear coating composition that is typically applied to the interior of automobiles and trucks.

The novel coating composition may be used as a base coat or as a pigmented monocoat topcoat. Both of these compositions require the presence of pigments. Typically, a pigment-to-binder ratio of 0.1/100 to 200/100 is used depending on the color and type of pigment used. The pigments are formulated into mill bases by conventional procedures, such as, grinding, sand milling, and high speed mixing. Generally, the mill base comprises pigment and a binder or a dispersant or both in a solventborne or aqueous medium. The mill base is added in an appropriate amount to the coating composition with mixing to form a pigmented coating composition.

Any of the conventionally-used organic and inorganic pigments, such as, white pigments, like, titanium dioxide, color pigments, metallic flakes, such as, aluminum flake, special effects pigments, such as, coated mica flakes, coated aluminum flakes and the like and extender pigments can be used. It may be desirable to add flow control additives.

The novel coating composition may be used as a primer or a sealer in which case typical pigments used in primers would be added, such as, carbon black, barytes, silica, iron oxide and other pigments that are commonly used in primers in a pigment-to-binder ratio of 10/100 to 300/100. These primers and sealers exhibit exceptional adhesion to untreated bare metal substrates, such as, aluminum and steel substrates, and to treated metal substrates, such as, galvanized steel, and provide excellent stone chip resistance.

The coating composition can be applied by conventional techniques, such as, spraying, electrostatic spraying, dipping, brushing, and flow coating.

The coating composition is particularly useful for the repair and refinish of automobile bodies and truck bodies and parts as a clear coat, pigmented base coat, mono-coat as a primer, sealer or primer surfacer.

The novel composition has also uses as binder for rapid cure chip coats. The novel composition of this invention can be combined with the isocyanate reagents described above directly without the use of a solvent or additional components and applied to an automobile body directly using application methods known in the art such as integrated multi-component applicators, spray guns or similar devices. Optionally, the combination of the composition of this invention including the typical isocyanate component under simple agitation forms a mass with a desired viscosity profile for direct application to a surface, e.g., a putty, using spatulas or other manual application devices, such as a squeegee.

The novel composition has uses for coating any and all items manufactured and painted by automobile sub-suppliers, frame rails, commercial trucks and truck bodies, including but not limited to beverage bottles, utility bodies, ready mix concrete delivery vehicle bodies, waste hauling vehicle bodies, and fire and emergency vehicle bodies, as well as any potential attachments or components to such truck bodies, buses, farm and construction equipment, truck caps and covers, commercial trailers, consumer trailers, recreational vehicles, including but not limited to, motor homes, campers, conversion vans, vans, large commercial aircraft and small pleasure aircraft, pleasure vehicles, such as, snow mobiles, all terrain vehicles, personal watercraft, motorcycles, and boats. The novel composition also can be used as a coating for industrial and commercial new construction and maintenance thereof; cement and wood floors; walls of commercial and residential structures, such as, office buildings and homes; amusement park equipment; concrete surfaces, such as parking lots and drive ways; asphalt and concrete road surface, wood substrates, marine surfaces; outdoor structures, such as bridges, towers; coil coating; railroad cars; printed circuit boards; machinery; OEM tools; signs; fiberglass structures; sporting goods; and sporting equipment.

The following are testing procedures used in the Examples:

Cotton Tack FreeTime

Allow coated panel to dry for set period of time (e.g. 30 minutes). Drop a cotton ball from a height of 1 inch onto the surface of the panel and leave the cotton ball on the surface for a set time interval and invert panel. Repeat above until the time the cotton ball drops off the panel on inversion and note that as the cotton tack free time.

MEK Rubs

A coated panel is rubbed (100 times) with an MEK (methyl ethyl ketone) soaked cloth using a rubbing machine and any excess MEK is wiped off. The panel is rated from 1–10. Rating 10—no visible damage to the coating, rating 9—1-3 distinct scratches, rating 8—4-6 distinct scratches, rating 7—7-10 distinct scratches, rating 6—10-15 distinct scratches with slight pitting or slight loss of color, rating 5—15-20 distinct scratches with slight to moderate pitting or moderate loss of color, rating 4—scratches start to blend into one another, rating 3—only a few undamaged areas between blended scratches, rating 2—no visible signs of undamaged paint, rating 1 complete failure—bare spots are shown. The final rating is obtained by multiplying the number of rubs by the rating.

Water Spot Test

Water spot rating is a measure of how well the film is crosslinked early in the curing of the film. If water spot damage is formed on the film, this is an indication that the cure is not complete and further curing of the film is needed before the film can be wet sanded or buffed or moved from the spray both. The water spot rating is determined in the following manner.

Coated panels are laid on a flat surface and deionized water was applied with a pipette at 1 hour-timed intervals. A drop about ½ inch in diameter was placed on the panel and allowed to evaporate. The spot on the panel was checked for deformation and discoloration. The panel was wiped lightly with cheesecloth wetted with deionized water, which was followed by lightly wiping the panel dry with the cloth. The panel was then rated on a scale of 1 to 10. Rating of 10 best—no evidence of spotting or distortion of discoloration, rating 9—barely detectable, rating 8—slight ring, rating 7—very slight discoloration or slight distortion, rating 6—slight loss of gloss or slight discoloration, rating 5—definite loss of gloss or discoloration, rating of 4—slight etching or definite distortion, rating of 3—light lifting, bad etching or discoloration, rating of 2—definite lifting and rating of 1—dissolving of the film.

BK Dry Time

Surface drying times of coated panels measured according to ASTM D5895-03.

Swell Ratio

The swell ratio of a free film (removed from a sheet of TPO—thermoplastic olefin) was determined by swelling the film in methylene chloride. The free film was placed between two layers of aluminum foil and using a LADD punch, a disc of about 3.5 mm in diameter was punched out of the film and the foil was removed from the film. The diameter of the unswollen film ($D_o$) was measured using a microscope with a 10× magnification and a filar lens. Four drops of methylene chloride were added to the film and the film was allowed to swell for a few second and then a glass slide was placed over the film and the swollen film diameter ($D_s$) was measured. The swell ratio was then calculated as follow:

$$\text{Swell Ratio} = (D_s)^2/(D_o)^2$$

Persoz Hardness Test

The change in film hardness of the coating was measured with respect to time by using a Persoz hardness tester Model No. 5854 (ASTM D4366), supplied by Byk-Mallinckrodt, Wallingford, Conn. The number of oscillations (referred to as Persoz number) were recorded.

Hardness (Fischer)

Hardness was measured using a Fischerscope® hardness tester (the measurement is in Newtons per square millimeter).

Gel Fraction

Measured according to the procedure set forth in U.S. Pat. No. 6,221,494 col. 8 line 56 to col. 9 line 2 which procedure is hereby incorporated by reference.

Time to Gel

The time in minutes it takes for a liquid coating to gel.

Direct to Metal Adhesion Test

Adhesion of a coating to bare metal substrates was determined according to ASTM D3359-02, the standard test method for measuring adhesion by tape test.

The present invention is further defined in the following Examples. It should be understood that these Examples are given by way of illustration only. From the above discussion and these Examples, one skilled in the art can ascertain the essential characteristics of this invention, and without departing from the spirit and scope thereof, can make various changes and modifications of the invention to adapt it to various uses and conditions. As a result, the present invention is not limited by the illustrative examples set forth herein below, but rather is defined by the claims contained herein below.

LC/MS (Liquid Chromatography/Mass Spectroscopy) analyses were performed on a Waters Alliance 2790 LC quipped with a MS (ES) interface. Column: Zorbax SB-C18, 2.1×150 mm at 50° C.; Solvents: A=99:1 water/acetonitrile, B=acetonitrile, C=methanol, D=80:20 acetonitrile/water; Conditions: 90% A/10% B/0.25% D to 0% A/100% B/0.25% D over 30 min, hold ten minutes, then return to initial conditions after 42 min; Wavelength: 191–799 nm; Flow rate: 0.25 mL/min.

GC/MS (Gas Chromatography/Mass Spectroscopy) M was performed on an Agilent 6890 gas chromatograph coupled with Agilent 5973 MSD. A J & W Scientific DB-5 capillary column was used. Helium was used as carrier gas. The GC chromatography was programmed to start at 70 C for 4 mins, followed by temperature ramping to 300 C at rate of 10 C/min, the final temperature was hold for 7 mins. The entire run time was 34 mins. 1.0 ul sample solution was injected to obtain the desired chromatography, ionization method is EI.

EXAMPLE 1

Hydroformylation of 2-methylbicyclo[2.2.1]hept-5-ene-2-carbonitrile

The hydroformylation catalyst was prepared by combining 0.31 g dicarbonylacetylacetonato rhodium(I) (1.2 mmol) and phosphite ligand (5.8 mmol) in 5 mL of toluene, forming under vigorous gas evolution a clear, yellow solution of phosphite acetylacetonato rhodium(I). The catalyst solution was added to 539 g of 2-methyl-bicyclo-[2.2.1]hept-5-ene-2-carbonitrile (4.05 mol) in 200 mL of toluene, and the whole reaction mixture was charged into a 1 L autoclave. The autoclave was heated to 85° C. and pressurized with 85 psig CO/$H_2$ mixture for about 16 h, while the progress of the reaction was periodically monitored by GC analysis. After venting the reactor, cooling to room temperature, and rinsing with methanol, solvent was removed from the reaction mixture by rotary evaporation, and the residual yellow oil was distilled in vacuo to yield 567.5 g of 5(6)-formyl-2-methylbicyclo[2.2.1]heptane-2-carbonitrile as colorless liquid (86% isolated yield). Boiling point: 99.6° C. at 0.5 Torr. GC/MS analysis revealed that the product was a mixture of several diastereomers.

EXAMPLE 2

A. Hydrogenation of (5 or 6)-formyl-2-methylbicyclo[2.2.1]heptane-2-carbonitrile (mixture of isomers) to (5 or 6)-(hydroxymethyl)-2-methylbicyclo [2.2.1]heptane-2-carbonitrile 416 g of (5 or 6)-formyl-2-methylbicyclo[2.2.1]heptane-2-carbonitrile (2.55 mol) was dissolved in 200 g THF (tetrahydrofuran), 20 g catalyst, 5% Ru on carbon (Aldrich), was added, and the whole reaction mixture was charged into a 1 L autoclave. The autoclave was heated to 90° C. and pressurized with 1000 psig $H_2$ gas for 12 h while the progress of the reaction was periodically monitored by GC analysis. After venting the reactor, cooling to room temperature, and rinsing with THF, the reaction mixture was filtered though a plug of celite under nitrogen. Solvent was removed from the reaction mixture by rotary evaporation, and the residual oil (388 g) was distilled in vacuo to yield 275 g (1.66 mol) of (5 or 6)-(hydroxymethyl)-2-methylbicyclo [2.2.1]heptane-2-carbonitrile as colorless liquid (65% isolated yield). Boiling point: 93.3° C. at 80 mTorr. The product was pure by GC/MS analysis.

B: Hydrogenation of (5 or 6)-(hydroxymethyl)-2-methyl-bicyclo[2.2.1]heptane-2-carbonitrile to ((5 or 6)-(aminomethyl)-5-methylbicyclo[2.2.1]heptan-2(3)-yl)methanol (Compound X)

435 g of (5 or 6)-(hydroxymethyl)-2-methylbicyclo-[2.2.1]-heptane-2-carbonitrile (2.63 mol) was dissolved in 150 mL methanol and 30 g catalyst slurry, Raney® 2700 cobalt slurry in water (Aldrich), was added. The reaction mixture was charged into a 1 L autoclave and 110 g ammonia (6.46 mol) was added. The autoclave was heated to 85° C. and pressurized with 1000 psig $H_2$ mixture for at least 12 h while the progress of the reaction was periodically monitored by GC/MS analysis. After venting the reactor, cooling to room temperature, and rinsing with methanol, the reaction mixture was filtered though a plug of silica under nitrogen, and the silica plug was rinsed with additional methanol. Solvent was removed from the reaction mixture by rotary evaporation, and the residual oil (389 g) was distilled in vacuo to yield 346 g (2.04 mol) of (5-(aminomethyl)-5-methylbicyclo[2.2.1]heptan-2(3)-yl)methanol (Compound X) as colorless, viscous liquid (78% isolated yield). Boiling point: 98° C. at 12 mTorr. The product was pure by GC/MS analysis.

EXAMPLE 3

A. Hydrogenation of 2-methyl-2-cyano-(5 or 6)-formyl-bicyclo[2.2.1]heptane to 2-methyl-2-cyano-(5 or 6)-hydroxymethyl-bicyclo[2.2.1]heptane To a 1 L pressure reactor were added 172 g starting nitrile-aldehyde, 8.2 g of ESCAT 440 5% Ru/C, and 345 g THF. The reactor was sealed, purged with hydrogen and tested for leaks. The reactor was heated to 90° C. at which point the pressure was increased to 4826 kPa (700 psig) with hydrogen and the reaction commenced. Hydrogen was constantly replenished from a cylinder and controlled by a forward pressure regulator. After 6.25 hours the reaction was cooled. A gas chromatogram of the product showed essentially full conversion to the nitrile alcohol and less than 5% high boiling products. An infrared spectrum of the product revealed no carbonyl stretching bands but the presence of O—H stretching at 3421 $cm^{-1}$. Nuclear magnetic resonance spectroscopy of the sample revealed the presence of nitrile (127 ppm) and hydroxyl-substituted methylene (66 ppm).

B. Hydrogenation of 2-methyl-2-cyano-(5 or 6)-hydroxymethyl-bicyclo[2.2.1]heptane to 2-methyl-2-methyleneamine-(5 or 6)-hydroxymethyl-bicyclo [2.2.1]heptane compound (X)

This is another procedure to form compound (X). To a 1 L pressure reactor were added 150 g of the product of example 2, 10 g of Raney® Co 2724, approximately 10 g water, and 150 g methanol (to aid in transfer). The reactor was sealed, purged with hydrogen and tested for leaks and cooled. Ammonia (250 g) was added by distillation from a cylinder. The reactor was heated to 85° C. at which point the pressure was increased to 6895 kPa (1000 psig) with hydrogen and the reaction commenced. Hydrogen was constantly replenished from a cylinder and controlled by a forward pressure regulator. While not essential, the reactor was maintained at temperature and pressure for 10 hours at which time it was cooled. A gas chromatogram of the sample showed nearly quantitative conversion to the desired amine-alcohol. An infrared spectrum of the product revealed no nitrile stretching absorbance (2235 $cm^{-1}$) but the presence of amine N—H stretching absorbances around 3377 and 3297 $cm^{-1}$. NMR spectra revealed the absence of any nitrile peaks in the 13C spectrum (~125 ppm) and the formation of compound (XII). The product was purified via distillation.

EXAMPLE 4

A: Hydrogenation of 3-ethyl-2-cyano-(5 or 6)-formyl-bicyclo[2.2.1]heptane to 3-ethyl-2-cyano-(5 or 6)-hydroxymethyl-bicyclo[2.2.1]heptane To a 100 cc pressure reactor were added 32.1 g starting nitrile-aldehyde, 1.7 g of ESCAT 440 5% Ru/C, and 20 g THF. The reactor was sealed, purged with hydrogen and tested for leaks. The reactor was heated to 100° C. at which point the pressure was increased to 3447 kPa (500 psig) with hydrogen and the reaction commenced. Hydrogen was constantly replenished from a 1-L reservoir and controlled by a forward pressure regulator. After nearly 6 hours the reaction was cooled. An infrared spectrum of the product revealed no carbonyl stretching bands but the presence of O—H stretching at 3424 $cm^{-1}$. Nuclear magnetic resonance spectroscopy of the sample revealed the presence of nitrile (124 ppm) and hydroxyl-substituted methylene (66–68 ppm).

B: Hydrogenation of 3-ethyl-2-cyano-(5 or 6)-hydroxymethyl-bicyclo[2.2.1]heptane to 3-ethyl-2-methyleneamine-(5 or 6)-hydroxymethyl-bicyclo [2.2.1]heptane compound (XIII)

To a 1 L pressure reactor were added 150 g of the product of example 3A, 10 g of Raney® Co 2724, approximately 10 g water, and 150 g methanol (to aid in transfer). The reactor was sealed, purged with hydrogen and tested for leaks and cooled. Ammonia (250 g) was added by distillation from a cylinder. The reactor was heated to 85° C. at which point the pressure was increased to 6895 kPa (1000 psig) with hydrogen and the reaction commenced. Hydrogen was constantly replenished from a cylinder and controlled by a forward pressure regulator. While not essential, the reactor was maintained at temperature and pressure for 10 hours at which time it was cooled. A gas chromatogram of the sample showed nearly quantitative conversion to the desired amine-alcohol. An infrared spectrum of the product revealed no nitrile stretching absorbance (2235 $cm^{-1}$) but the presence of amine N—H stretching absorbances around 3377 and 3297 $cm^{-1}$. NMR spectra revealed the absence of any nitrile peaks in the $^{13}C$ spectrum (~125 ppm) and the formation of compound (XIII). The product was purified via distillation.

EXAMPLE 5

Synthesis of compound represented by formula (XXII).

To a four-necked 1000 mL round bottom flask fitted with magnetic stirrer, thermocouple, condenser and addition funnel was added under nitrogen atmosphere 50.9 g of 6-amino-1-hexanol (97%, 0.43 mol) followed by 450 mL of dry methylene chloride. Then 99.1 g (0.43 mol) di-secbutyl maleate was slowly added via the addition funnel while maintaining the temperature below 20° C. The pale yellow reaction mixture was stirred at room temperature over night, and the progress of the reaction was monitored by GC (disappearance of 6-amino-1-hexanol) and LC analysis. The reaction mixture was concentrated to about 200 mL, filtered on a medium frit to remove haze (di-secbutyl fumarate), then solvent was removed in vacuo to constant weight, yielding 149.1 g of a yellow, clear oil. LC/MS analysis: 12.94 min (M+H=346, 93.3%); 14.08 min (M+H=617, 2.3%, double addition product); 21.06 min (M+H=501, 2.0%, transesterification product).

EXAMPLE 6

Synthesis of compound represented by formula (XXV).

To a glass vial with magnetic stirrer was added under nitrogen atmosphere 6.2 g of (4-(aminomethyl)cyclohexyl) methanol (0.04 mol). The vial was cooled to 0° C. and 9.9 g (0.04 mol) di-secbutyl maleate was slowly added via pipette. The reaction mixture was placed in a heating block and stirred at 50° C. room temperature over night, and the progress of the reaction was monitored by GC (disappearance of starting materials) and LC analysis. The aspartic aminoalcohol XXV was obtained as clear oil in quantitative yield. LC/MS analysis: 14.11, 14.44 min (M+H=372, 18.1%, 48.3%); 20.16 min (M+H=614, 29.7%, unknown).

EXAMPLE 7

Synthesis of compound represent by formula (XXIX).

To a four-necked 1 L round bottom flask fitted with magnetic stirrer, thermocouple, condenser and addition funnel was added under nitrogen atmosphere 148.7 g of (5-(aminomethyl)-5-methyl-bicyclo-[2.2.1]-heptan-2(3)-yl)methanol (0.879 mol) and 200 mL of dry acetonitrile. The solution was cooled to 0° C. and 151.3 g diethylmaleate (0.879 mol) (maleic acid diethylester, Aldrich) was added dropwise over 40 minutes while maintaining the temperature below 3° C. The reaction mixture was then allowed to warm up to room temperature and stirred for three days, while the progress of the reaction was monitored by GC (disappearance of starting materials) and LC/MS analysis. Solvent was removed by rotary evaporation, and the residual colorless oil (299.2 g) was dried in vacuo. 190.3 g of (XXIX) was isolated as colorless oil after solvent removal and filtration through celite. GC analysis: 22.04, 22.12, 22.41 min (23.6%, 14.9%, 58.4%, all AAO 2). LC/MS analysis (ES) confirms exclusively desired product (M+H=342.3), no primary or tertiary amine detected.

EXAMPLE 8

Synthesis of compound represented by formula (XXX).

To a four-necked 250 mL round bottom flask fitted with magnetic stirrer, thermocouple, condenser and addition funnel was added under nitrogen atmosphere 70.8 g of (X) (0.418 mol). Then 99.4 g (0.418 mol) dibutyl maleate (Aldrich) was slowly added via the addition funnel while the temperature gradually increased to about 50° C. The reaction mixture was then heated to 70° C. for about 24 h, while the progress of the reaction was monitored by GC and LC analysis. After cooling to room temperature, 166.0 g of the desired product (XXX) was obtained as clear and colorless oil.

LC/MS analysis confirms desired product (M+H=398.3) in>97% purity.

EXAMPLE 9

Synthesis of compound represented by formula (XXXI).

To a four-necked 500 mL round bottom flask fitted with magnetic stirrer, thermocouple, condenser and addition funnel was added under nitrogen atmosphere 100.0 g of (5-(aminomethyl)-5-methyl-bicyclo-[2.2.1]-heptan-2(3)-yl) methanol (0.59 mol). Then 134.9 g (0.59 mol) di-secbutyl maleate was slowly added via the addition funnel while the temperature gradually increased to about 44° C. The reaction mixture was then heated to 70° C. for 60 hours, while the progress of the reaction was monitored by GC (disappearance of starting materials) and LC analysis. After cooling to room temperature, 229.5 g of di-sec-butyl 2-((5-(hydroxymethyl)-2-methylbicyclo[2.2.1]heptan-2-yl)-methylamino)-succinate was obtained as pale yellow, clear oil. LC/MS analysis: 13.76 min, 14.58 min (M+H=398.3).

EXAMPLE 10

Synthesis of compound represented by formula (XXXII).

To a four-necked 2 L round bottom flask fitted with magnetic stirrer, thermocouple, condenser and addition funnel was added under nitrogen atmosphere 187.1 g of dicyclohexyl-maleate (0.667 mol) (maleic acid dicyclohexylester) and 800 mL of dry acetonitrile. 112.9 g of (5-(aminomethyl)-5-methyl-bicyclo-[2.2.1]-heptan-2(3)-yl) methanol (0.667 mol) was slowly added via the addition funnel, which was gently heated to facilitate the addition of the viscous liquid, and finally rinsed with a few mL of acetonitrile. The solution was heated to 50° C. and stirred for 60 hours, while the progress of the reaction was monitored by GC (disappearance of starting materials) and LC/MS analysis. Solvent was removed by rotary evaporation yielding a yellow oil (299.9 g). The crude material was purified by flash chromatography on silica gel (10% ethyl acetate in hexane). 208.2 g of (XXXII) was isolated as highly viscous and hazy liquid after solvent removal and filtration through celite. GC analysis: 19.46 min (0.4%, Cy maleate); 20.09 min (3.2%, Cy fumarate); 28.68, 29.06, 29.52 min (5.5%, 34.0%, 55.8%). LC/MS analysis (ES) confirms exclusively desired product (M+H=450.2), no primary or tertiary amine detected.

EXAMPLE 11

Synthesis of compound represented by formula (XXXIII).

To a four-necked 1 L round bottom flask fitted with magnetic stirrer, thermocouple, condenser and addition funnel was added under nitrogen atmosphere 64.0 g of dicyclohexyl-maleate (0.228 mol) (maleic acid dicyclohexylester), 400 mL of dry acetonitrile and 46.0 g compound (XVI) (0.254 mol). The solution was heated to 60° C. and stirred for about 24 h, while the progress of the reaction was monitored by GC and LC/MS analysis. The reaction mixture was filtered through a medium frit before solvent was removed by rotary evaporation yielding (XXXIII) as a colorless oil (111.2 g). GC analysis: 15.10, 15.29, 15.49 min; 19.49 min (1.0%, Cy maleate); 20.14 min (15.1%, Cy fumarate); 32.00, 32.53, 33.80 min LC/MS (ES) confirms desired product (M+H=462.3, ca. 93% by MS).

The Brookfield viscosity of a solution of commercial available diamine, Desmophen® NH-1420 (Bayer), to the viscosity of NCO reactive components XXIX (Example 6) and XXX (Example 7) were compared.

The results are as follows:

| NCO reactive component/composition | Brookfield Viscosity |
|---|---|
| Des. NH1420 Composition | 1000 cps |
| XXIX (Ex. 6) Composition | 514 cps |
| XXX (Ex. 7) Composition | 665 cps |

Desmophen® NH-1420—reaction product of 4,4'-methylene-biscyclohexanamine and diethyl maleate (Bayer—1000 cps).

These viscosity measurements show a much lower viscosity of the NCO Reactive Component (XXIX) and (XXX) of this invention in comparison to the viscosity of Desmophen® NH-1420 (Bayer). The high viscosity of Desmophen® NH-1420 requires the use of low viscosity, reactive diluents, such as, ketimines for the formulation of true 2.1 VOC systems. Because of the surprisingly low viscosity of a number of the NCO reactive components (aspartic amino-alcohols) of this invention, they can be formulated without the addition of reactive diluents.

EXAMPLE 12

Coating compositions 12A–12E were prepared as follows:

| Coating Composition | 12A | 12B | 12C | 12D | 12E |
|---|---|---|---|---|---|
| Portion 1 | | | | | |
| NCO Reactive Component (XXIX) Example 7 | 20 | — | — | — | — |
| NCO Reactive Component (XXX) Example 8 | — | 20 | — | — | — |
| NCO Reactive Component (XXXI) Example 9 | — | — | 19.72 | — | — |
| NCO Reactive Component (XXII) Example 5 | — | — | — | 15 | — |
| NCO Reactive Component (XXXII) Example 10 | — | — | — | — | 20 |
| Butyl Acetate | 14.86 | 13.64 | 14.20 | 9.84 | 13.56 |
| Flow Additive[1] | 0.48 | 0.44 | 0.39 | 0.32 | 0.38 |
| Catalyst Solution[2] | 4.48 | 4.43 | 1.96 | 3.20 | 1.88 |
| Acetic Acid | 0.58 | 0.53 | 0.24 | 0.38 | 0.23 |
| Portion 2 | | | | | |
| Tolonate ® HDT[3] | 28.43 | 24.43 | 19.46 | 17.05 | 17.45 |

[1]Flow additive—20% BYK 301 ® flow additive, supplied by BYK CHEMIE, in propylene glycol monomethyl ether acetate.
[2]Catalyst Solution—1% DBTDL (dibutyl tin dilaurate) in methyl ethyl ketone.
[3]Tolonate HDT—isocyanurate trimer of hexamethylene diisocyanate supplied by Rhodia Inc.

For each of Examples 12A–12E, the constituents of Portion 1 were charged into a mixing vessel and then Portion 2 was charged into the mixing vessel and thoroughly mixed with Portion 1. Each of the coating compositions 12A–12E was applied with a doctor blade over a separate phosphated cold roll steel panel primed with a layer of PowerCron® Primer supplied by PPG, Pittsburgh, Pa., to a dry coating thickness of about 50 micrometers and air dried at ambient temperature conditions. Then the panels were tested using the test set forth in following Table 2 and the results of the test are shown in this table.

TABLE 2

| Coating Composition | 12A | 12B | 12C | 12D | 12E |
|---|---|---|---|---|---|
| NCO Reactive Comp. | XXIX | XXX | XXXI | XXII | XXXII |
| Theo. Eq. Wt. | 171 | 199 | 199 | 172.7 | 225 |
| Calculated Wt. Solids | 70% | 70% | 70% | 70% | 70% |
| Time to gel (min.) | 114 | 150 | 101 | 150 | 83 |
| BK 3 time (min.) | 86.2 | 75.6 | 111 | 73.23 | 151 |
| BK 4 time (min.) | 354 | 99 | 475 | 108.66 | 210 |
| Cotton tack free time (min.) | 114 | 69 | 180 | 105 | >300 |
| Water spot - 4 hrs. @ Room. Temp. | 8 | 8 | 9 | 9 | 8 |
| MEK rubs - 4 hrs @ Room Temp. | 600 | 800 | 600 | 100 | 750 |
| Swell Ratio - 1 day @ Room Temp. | 1.93 | 1.99 | 1.93 | 1.87 | 1.90 |
| Swell Ratio - 30 day @ Room Temp. | 1.90 | 1.99 | 1.87 | 1.96 | 1.82 |
| Persoz hardness - 4 hrs @ Room Temp. | 20 | 30 | 19 | 27 | 18 |
| Fischer Hardness - 1 day @ Room Temp. | 9.40 | 14.85 | 11.00 | 13.80 | 4.70 |
| Fischer Hardness - 30 days @ Room Temp. | 30.8 | 70.0 | 44.0 | 23.3 | 13.4 |
| Gel Fraction - 30 days @ Room Temp. | 94.78 | 95.00 | 93.54 | 95.23 | 87.83 |

Theo. Eq. Wt.—theoretical equivalent weight.
Min—minutes

The results for coating compositions 12A–12E show that coatings made from the NCO Reactive Components of this invention have excellent early cure, as is evident from the short BK dry times, excellent early water spot, and good MEK rubs at 4 hours and remain fluid for a useful period of time. NCO Reactive Compound (XXX) is particularly useful with a time to gel of 150 minutes and good early cure. The films also have excellent final properties such as hardness and gel fraction.

EXAMPLE 13

Coating compositions 13A–13D were prepared as follows:

| Coating Composition | 13A | 13B | 13C | 13D |
|---|---|---|---|---|
| Portion 1 | | | | |
| NCO Reactive Component (XXX) Example 8 | 20 | 20 | 20 | 20 |
| Butyl acetate | 15.6 | 12.14 | 12.63 | 15.79 |
| Flow Additive (described in Ex. 12) | 0.44 | 0.44 | 0.44 | 0.44 |
| Portion 2 | | | | |
| Tolonate ® HDT (described in Ex. 12) | 19.73 | 19.73 | 19.73 | 19.73 |
| Portion 3 | | | | |
| Catalyst Solution (described in Ex. 12) | 0.99 | 3.97 | 0 | 0 |
| Acetic acid | 0 | 0.48 | 0 | 0 |
| 10% DABCO[4] in xylene | 0 | 0 | 3.96 | 0 |
| 25% DMEA[5] in methyl ethyl ketone | 0 | 0 | 0 | 0.8 |

[4]DABCO—1,4-diazabicyclo(2.2.2)octane
[5]DMEA—dimethyl ethanol amine

For each of Examples 13A–13D, the constituents of Portion 1 were charged into a mixing vessel in the order shown above and mixed then Portion 2 was charged into the mixing vessel and thoroughly mixed with Portion 1. Portion 3 was then added with mixing. Each of the coating compositions was applied with a doctor blade over a separate phosphated cold roll steel panel primed with a layer of PowerCron® Primer supplied by PPG, Pittsburgh, Pa., to a dry coating thickness of about 50 micrometers and air dried at ambient temperature conditions. A second set of panels were cured for 20 minutes at 60° C. Then the panels were tested using the test set forth in following table and the results of the test are shown in Table 3 below.

TABLE 3

| Coating Composition | 13A | 13B | 13C | 13D |
|---|---|---|---|---|
| NCO Reactive Comp. | XXX | XXX | XXX | XXX |
| Theo. Eq. Wt. | 199 | 199 | 199 | 199 |
| Calculated Wt. Solids | 70% | 70% | 70% | 70% |
| Catalyst (on binder) | 250 ppm DBTDL | 1000 ppm DBTDL & 1.2% acetic acid | 1% DABCO | 0.5% DMEA |
| Time to gel (min.) | 51 | 84 | 146 | 193 |
| BK 3 time (min.) | 319 | 98 | 63.8 | 260 |
| BK 4 time (min.) | >692 | 239 | 201 | >633 |
| Water spot - 4 hrs. @ Room. Temp. | 7 | 9 | 9 | 5 |
| MEK rubs - 4 hrs @ Room Temp. | 300 | 600 | 700 | 400 |
| Persoz Hardness - 4 hrs @ Room Temp. | 19 | 8 | 33 | tacky |
| Persoz Hardness - 20 min. @ 60° C. bake on cool down | 243 | 35 | 101 | 130 |
| Fischer Hardness - 1 day @ Room Temp. | 38.6 | 8.2 | 9.4 | 31 |
| Fischer Hardness - 30 days @ Room Temp. | 75.3 | 25.2 | 11.3 | 55.0 |
| Fischer Hardness - after 20 min @ 60° C. on cool down | 94 | Too soft | 2.1 | 29 |
| Fischer Hardness - 1 day after 20 min @ 60° C. | 145 | 8.11 | 19 | 79 |
| Fischer Hardness - 30 days after 20 min @ 60° C. | 86.1 | 31 | 17 | 104 |

Theo. Eq. Wt.—theoretical equivalent weight
ppm—parts per million
ml—minutes

Coating compositions 13A–13D show that compositions made from the NCO Reactive Components of this invention may be catalyzed by a variety of catalysts, including tertiary amines. The systems made using DABCO and DMEA have excellent early cure, as is evident from the short BK dry times, excellent early water spot, and good MEK rubs at 4 hours and have a significantly long time to gel (146 to 193 minutes). These types of catalysts are particularly useful when curing at slightly elevated temperatures for short times, such as, 20 minutes at 60° C. The films also have good final properties, such as, hardness.

EXAMPLE 14

Direct-to-Metal Adhesion

In the following Example, the reactive isocyanate compound XXXI was combined with Desmodur® 3300 and 250 ppm DBTDL at 70% weight in butyl acetate in a 30 mm vial and vortexed for 20 seconds. The coating composition was applied with a doctor blade (5 mil film) over A) clean, unpolished aluminum, B) clean, unpolished cold roll steel, and C) clean, unpolished galvanized steel. The adhesion of the coating film was measured according to the aforementioned "X-hatch" tape test after 1 day, 3 days and seven days. The results are summarized in the attached table, showing excellent adhesion (10=highest rating) for cold roll steel and galvanized steel, and almost the same excellent adhesion to aluminum.

| Compound XXXI ||||||
|---|---|---|---|---|---|
| Day 1 Plates | Tape used | Rating | Day 3 Plates | Rating | Day 7 Plates | Rating |
| A | 898 | 9 | A | 9 | A | 9 |
| B | 898 | 10 | B | 10 | B | 10 |
| C | 898 | 10 | C | 10 | C | 10 |

The invention claimed is:

1. A hydroxy amine compound having a structure selected from at least one of the following formulae (VI) to (XIX):

(VI)

(VII)

(VIII)

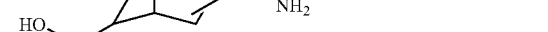

(IX)

(X)

(XI)

(XII)

(XIII)

-continued
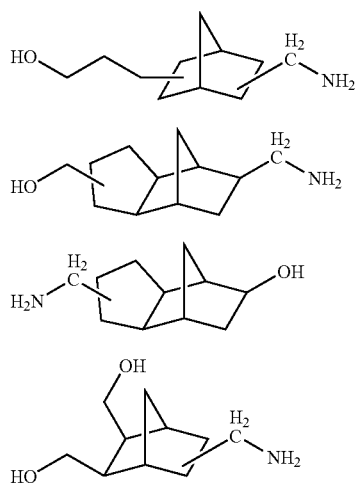
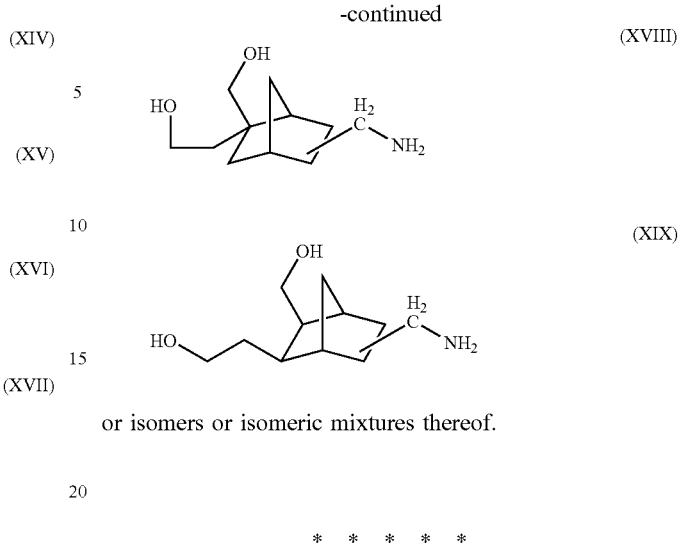
or isomers or isomeric mixtures thereof.
* * * * *